US006323191B1

(12) United States Patent
Harris et al.

(10) Patent No.: US 6,323,191 B1
(45) Date of Patent: Nov. 27, 2001

(54) SMALL MOLECULE CHLORIDE TRANSPORT

(75) Inventors: David J. Harris, Lexington; Edward R. Lee, Natick; Canwen Jiang, Marlboro; Seng H. Cheng, Wellesley; Mathieu Lane, Cambridge, all of MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 09/334,936

(22) Filed: Jun. 17, 1999

Related U.S. Application Data

(60) Provisional application No. 60/089,880, filed on Jun. 19, 1998.

(51) Int. Cl.$^7$ .................... A01N 45/00; A01N 43/04; A01N 37/00; A61K 31/56; A61K 31/70

(52) U.S. Cl. ................ 514/169; 514/44; 514/51; 514/170; 514/557; 514/581; 514/851

(58) Field of Search ................ 514/169, 170, 514/581, 44, 51, 557, 851

(56) References Cited

U.S. PATENT DOCUMENTS

| | | |
|---|---|---|
| 4,943,624 | 7/1990 | Regen . |
| 5,179,190 | 1/1993 | Regen et al. . |
| 5,384,128 | 1/1995 | Meezan et al. . |
| 5,512,269 | 4/1996 | Molina y Vedia et al. . |
| 5,583,239 | 12/1996 | Regen . |
| 5,606,038 | 2/1997 | Regen . |
| 5,651,957 | 7/1997 | Molina y Vedia et al. . |
| 5,683,675 | 11/1997 | Molina y Vedia et al. . |
| 5,716,931 | 2/1998 | Molina y Vedia et al. . |
| 5,750,571 * | 5/1998 | Cheng et al. . |

FOREIGN PATENT DOCUMENTS

| | | |
|---|---|---|
| WO 9004401 | 5/1990 | (WO) . |
| WO 9632404 | 10/1996 | (WO) . |
| WO 94/28726 | 12/1996 | (WO) . |
| WO 9638464 | 12/1996 | (WO) . |
| WO 98 19682 A | 5/1998 | (WO) . |

OTHER PUBLICATIONS

Am. J. Physjol. 275 (1, Pt. 1), C171–C178. Jiang C et al. Partial restoration of cAMP–stimulated channel activity in delta F508 cells by deoxyspergualin, Apr. 14, 1998.*

Jiang, C. et al., "Correction Of Defective Chloride Secretion In CF Airway Cells In Vitro And In Vivo By GL–172", American Journal of Respiratory and Critical Care Medicine, vol. 159, No. 3, Mar. 1999, p. A678.

Merritt, M. et al., "Sterol–Polyamine Conjugates As Synthetic Ionophores", Journal of the American Chemical Society, vol. 120, No. 33, Aug. 1998, pp. 8494–8501.

El–Etri, M. et al., "Metalloporphyrin Chloride Ionophores: Induction Of Increased Anion Permeability In Lung Epithelial Cells", American J. Physiol., vol. 270, No. 3, Part 1, (1996), pp. L386–L392.

Welsh, M.J., "Effect Of Phorbol Ester And Calcium Ionophore On Chloride Secretion In Canine Tracheal Epithelium", American J. Physiol., vol. 253, No. 6, Part 1, (1987) pp. C828–C834.

Mehta et al., Polymerized Phospholipid Vesicles Containing Amphotericin B: Evaluation of Toxic and Antifungal Activities in vitro, *J. of Pharmaceutical Sciences*, 75 (6), pp. 579–581 (1986).

Fyles et al., Pores Formed by Bis–macrocyclic Bola–amphiphiles in Vesicle and Planar Bilayer Membranes, *J. Org Chem*, 61, pp. 8866–8874 (1996).

Kikuchi et al, Antimicrobial Activities of Squalamine Mimics, *Antimicrobial Agents and Chemotherapy*, 41 (7), pp. 1433–1438 (1997).

Sakai et al., Transmembrane Ion Transport Mediated by Amphiphilic Polyamine Dendrimers, *Tetrahedron Letters*, 38 (15) pp. 2613–2616 (1997).

Naka et al, Molecular Harpoons. Membrane–Disruptive Surfactants That Can recognize Osmotic Stress in Phospholipid Bilayers, *J. Am. Chem. Soc.*, 115, pp. 2278–2286 (1993).

Nagawa et al., Membrane–Disruptive Surfactants that are Highly Selective Toward Lipid Bilayers of Varying Cholesterol Content, *J. Am. Chem. Soc.*, 113, pp. 7237–7240 (1991).

Stadler; et al., Amphotericin B Mimics: A Sterol–Based Ionophore, *J. Am. Chem. Soc.*, 116, pp. 6677–6682 (1994).

Moore et al., Squalamine: AN Aminosterol Antibiotic from the Shark, *Proc. Natl. cad. Sci. USA*, 90, pp. 1354–1358 (1993).

Sadownik et al., Rapid Construction of a Squalamine Mimic, *J. Am Chem. Soc.*, 117, pp. 6138–6139 (1995).

Deng et al., Kinetic Evidence for Duplicity in Ion Transport, *J. Am. Chem. Soc.*, 118, pp. 8975–8976 (1996).

(List continued on next page.)

*Primary Examiner*—Leon B. Lankford, Jr.
*Assistant Examiner*—Michele C. Flood
(74) *Attorney, Agent, or Firm*—Finnegan, Henderson, Farabow, Garrett, & Dunner, L.L.P.

(57) ABSTRACT

Cystic fibrosis transmembrane conductance regulator (CFTR) is a chloride (Cl$^-$) channel regulated by phosphorylation and intracellular nucleotides. CFTR is the major Cl$^-$ transport pathway in airway epithelial cells. The abnormal transepithelial Cl$^-$ transport and subsequent defective fluid transport caused by CF is a result of the genetic mutations of the gene coding for the CFTR protein. The present invention is directed to the novel use of ionophores as artificial Cl$^-$ transport pathways into CF epithelia to treat the defective Cl$^-$ and fluid transport ionophores and in particular, small molecule ionophores, represent a potential novel means of treating CF. The invention also includes using an ionophore to generate chloride secretion on intact monolayers of airway epithelia cells and other epithelia cells by administering an ionophore to a mammal.

15 Claims, 8 Drawing Sheets

OTHER PUBLICATIONS

Quinton, Cystic Fibrosis: A Disease in Electrolyte Transport, *Faseb J.*, 4, pp. 2709–2717 (1990).

Jiang et al., Altered Fluid Transport Across Airway Epithelium in Cystic Fibrosis, *Science*, 262, pp. 424–427 (1993).

Smith et al., Cystic Fibrosis Airway Epithelia Fail to Kill Bacteria Because of Abnormal Airway Surface Fluid, *Cell*, 85, pp. 229–236 (1996).

Welsh et al., Molecular Mechanisms of CFTR Chloride Channel Dysfunction in Cystic Fibrosis *Cell*, 73, pp. 1251–1254 (1993).

Deng et al, A Synthetic Ionophore that Recognizes Negatively Charged Phospholipid Membranes *JACS*, 118, pp. 8975–8976 (1996).

* cited by examiner

SCHEME 2.

SMALL MOLECULE CHLORIDE TRANSPORT

The application claims the benefit of U.S. provisional application No. 60/089,880, filed Jun. 19, 1998.

The present invention relates to a novel method of treating cystic fibrosis. More particularly, the present invention relates to the use of artificial chloride channels or transporters as a therapeutic for cystic fibrosis. The invention also relates to a method of increasing cell membrane halide permeability.

Cellular lipid bilayers are highly impermeable to charged molecules. However, ionophores can increase the permeability of cell membranes to specific inorganic ions. For example, the antibiotic valinomycin complexes with potassium ions ($K^+$) and readily passes through the cell membrane. In the absence of valinomycin, $K^+$ passes through the cell membrane very slowly. Ionophores, which may be small hydrophobic molecules that dissolve in lipid bilayers, enable ions to be transported across the cellular bilayer because they form lipid-soluble complexes with specific ions.

The two classes of ionophores, mobile ion carriers and channel formers, operate by shielding the charge of the transported ion enabling the charged molecule to penetrate the hydrophobic interior of the cellular wall. Valinomycin, a mobile ion carrier, picks up $K^+$ on one side of the membrane, diffuses across the bilayer, and releases $K^+$, on the other side. Gramicidin A, a channel-forming ionophore, forms a transmembrane channel across the bilayer, which selectively allows ions to flow through the channel and across the bilayer.

Many ionophores are useful as antibiotics because in addition to transporting ions, the ionophore disrupts the cell membrane which leads to leakage of vital cellular constituents and cell destruction. There has recently been a great deal of interest in the design and synthesis of ionophores and other membrane disrupting compounds in the search for novel antibiotic agents. A well studied example is Amphotericin B (Amp B) (Nagawa et al., *J. Am. Chem. Soc.*, 113, pp. 7237–7240 (1991)). Amp B is an ionophore that generates transmembrane pores. These pores, which allow leakage of vital cellular constituents and trigger cell destruction, make Amp B an effective antibiotic. Subsequently, the structural elements of Amp B have become a starting point for designing compounds with similar functional characteristics. Many of these compounds, such as 5-Androstene-3B, 17B-bis[(oxycarbonyl) hexaethylene Glycol], also possess interesting ionophoric characteristics (Stadler, et al, *J. Am. Chem. Soc.*, 116, pp. 6677–6682 (1994)).

The antibiotic squalamine is a novel sterol-spermidine conjugate that has recently been isolated from tissues of the dogfish shark, Squalus acanthias (Moore et al., *Proc. Natl. Acad. Sci. USA*, 90, pp. 1354–1358 (1993)). This steroid, which is an adduct between spermidine and an anionic bile salt intermediate, has demonstrated potent antibacterial activity against both gram-negative and gram-positive bacteria. Unfortunately, squalamine is only found in limited quantities in nature.

In the search for compounds functionally equivalent to Amp B, several mimics of squalamine have been synthesized (Sadownik, et al., *J. Am. Chem. Soc.*, 117, pp. 6138–6139 (1995)). The sterol-spermine conjugates that have been made are both structurally similar to squalamine and demonstrate extraordinary antibiotic properties. The compounds' ability to exhibit potent activity against a broad spectrum of microorganisms are of particular interest. European patent application nos. WO 9638464, WO 9632404, and WO 9004401 describe the utility of this class of compounds as an antibiotic, the disclosures of which are hereby incorporated by reference.

In addition to their broad antibiotic activity, the synthetic mimics of squalamine possess the unique ionophoric activity of cell membrane and transport anion selectivity (Deng, et al., *J. Am. Chem. Soc.*,118, pp.8975–8976 (1996)). The transport of ions across negatively charged bilayers is favored over transport across neutral ones; and no $Na^+$ transport activity is observed while effective $Cl^-$ transport activity is observed.

Cystic fibrosis (CF) is a complex disease affecting many organs with epithelial cell linings. The lethal genetic disorder, caused by the presence of mutations in the gene that encodes for a protein known as cystic fibrosis transmembrane conductance regulator (CFTR), affects the permeability of the epithelial cell linings to $Cl^-$ ions. (Welsh et al., *Neuron*, 8, 821–829 (1992)). CFTR regulates the passage of $Cl^-$ ions through the cell membrane epithelial cells. (Quinton, *FASEB J.*, 4, 2709–2717 (1990); Jiang et al., *Science*, 262, 424–427 (1993); Smith et al., *J. Clini. Invest.*, 91, 1590–1597 (1994)). Through the regulation of ions across the cell membrane of epithelial cells, CFTR regulates the flow of fluid. In CF, the mutations of the CFTR gene cause defective transepithelial $Cl^-$ transport and therefore defective fluid transport.

The genetic mutations causing abnormal ion transport lead to abnormal mucous secretion, inflammation, infection and tissue damage. It is believed that CFTR regulates active ion transport-mediated fluid transport in a variety of epithelial cells including sweat glands, pancreas, intestine, genital tract, and airways. In airway epithelia, for example, it is believed that defective electrolyte and fluid transport causes impairment of airway clearance and defective bactericidal activity of salt-sensitive defensins, which subsequently results in recurrent infections and destruction of lungs in CF patients. (Jiang et al., *Science*, 262, 424–427 (1993); Smith et al., *Cell*, 85, 229–236 (1996); Goldman et al., *Cell*, 88, 553–560 (1997)). Patients suffering from CF are prone to recurrent lung infections and airway blockage, small bowel obstruction, pancreatic insufficiency, cirrhosis of the liver due to biliary tract obstruction, infertility in males, and eventually death.

Several therapeutic approaches are being developed concurrently for the treatment of CF. These include 1) use of agents that improve the anti-bacterial activity and viscosity of the mucous fluid lining the airways (Smith et al., *Cell*, 85, 229–236 (1996); Goldman et al., *Cell*, 88, 553–560 (1997)), 2) use of agents that activate alternative $Cl^-$ channels to compensate the CFTR $Cl^-$ channel defect, 3) protein and gene augmentation therapy. (Welsh et al., *Cell* 73, 1251–11254, 1993.), and 4) use of agents that reverse the mutant phenotype. There is currently no effective treatment for the disease.

Accordingly, the present invention is directed to the novel use of ionophores as artificial $Cl^-$ transport pathways in CF epithelia to treat the defective $Cl^-$ and fluid transport. Ionophores and in particular non-peptide ionophores, and in particular, small molecule ionophores, represent a potential novel means of treating CF. Preferred small molecule ionophores have a molecular weight less than or equal to 2000, or preferably less than or equal to 1750, or more preferably less than or equal to 1500, or even more preferably, less than or equal to 1000. To achieve these and other advantages and in accordance with the purpose of the invention, as embodied and broadly described, the invention treats CF by administering an effective amount of an ionophore to a patient.

In another aspect, the invention includes using an ionophore to generate chloride secretion on intact monolayers of airway epithelia cells and other epithelia cells by administering an ionophore to a mammal. Defective Cl⁻ secretion in airway epithelia in vitro and in vivo can be corrected.

In a further aspect, the invention includes using an ionophore to increase cell membrane halide and anion permeability of epithelia cells by administering an ionophore to a mammal.

The present invention also relates to novel ionophores that may be useful as artificial Cl- transport pathways; that may generate chloride secretion on intact monolayers of epithelia cells; and may increase cell membrane halide permeability.

The invention also provides for pharmaceutical compositions of ionophores as the free compound, or as a pharmaceutically acceptable salt thereof. Additionally the ionophores of the present invention may be the active ingredient in a pharmaceutical composition that includes carriers, fillers, extenders, dispersants, creams, gels, solutions and other excipients that are common in the pharmaceutical formulatory arts.

In a further aspect, the invention provides methods of administering the ionophores and the pharmaceutical compositions of the present invention by intravenous, oral, instillation, inhalation, topical, intraperitoneal, subcutaneous, or intramuscular routes. The ionophores and the pharmaceutical compositions may be administered, for example, in the form of capsules, powders, tablets, liquids, solutions, and aerosolized solutions. Also within the practice of the invention are methods of treating diseases or other conditions in a mammal that give rise to defective anion transport across cell membranes.

Additional features and advantages of the invention will be set forth in the description which follows, and in part will be apparent from the description, or may be learned by practice of the invention. The objectives and other advantages of the invention will be realized and attained by the method particularly pointed out in the written description and claims herein as well as the appended drawings.

This invention is directed to a method of treating CF by administering an effective amount of an ionophore to a patient. The method is useful in correcting the chloride imbalance in a cystic fibrosis patient. The practice of the invention is not to be limited as to theory.

In the practice of the invention, ionophores, preferably small molecule ionophores, selectively transport anions across lipid bilayers. Advantageously, the ionophores form an artificial Cl⁻ channel that increases cell membrane halide permeability. It was known that mimics of squalamine, GL-172 for example (See FIG. 1), favor transport of ions across negatively charged lipid bilayers and are not effective transporting cationic ions such as Na⁺ across lipid bilayers. See Deng, *JACS*, 118, 8975–8976 (1996). There was, however, based on Deng's work, no reasonable basis for predicting that mimics of squalamine or other ionophores could be effective in correcting the chloride imbalance in a cystic fibrosis patient.

CFTR is the major Cl⁻ transport pathway in airway epithelial cells. The abnormal transepithelial Cl⁻ transport and subsequent defective fluid transport caused by CF is a result of the genetic mutations of the gene coding for the CFTR protein. It is believed that in airway epithelia, defective ion and fluid transport leads to impairment of airway mucociliary clearance and defective bactericidal activity of salt-sensitive defensins, subsequently resulting in recurrent infections and destruction of lungs in CF patients. According to the practice of the invention, administering ionophores to CF epithelia forms artificial Cl⁻ transport pathways in the epithelia cells. The introduction of artificial Cl⁻ transport pathways treats the abnormal fluid transport.

Figure 1:
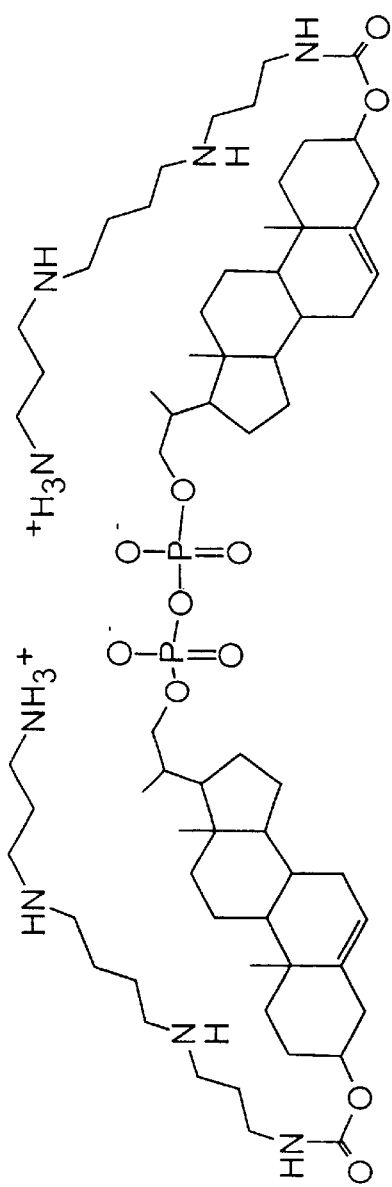
FIG. 1. depicts representative small molecule ionophores.
Figure 1:
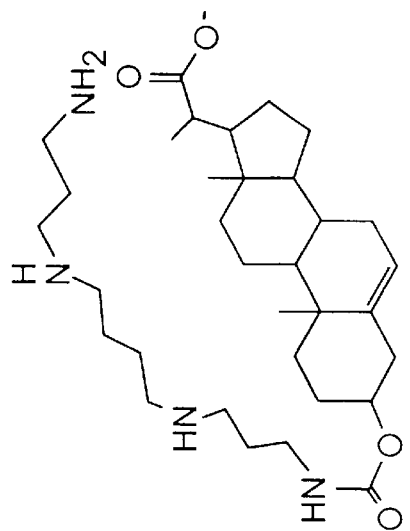
Figure 1:
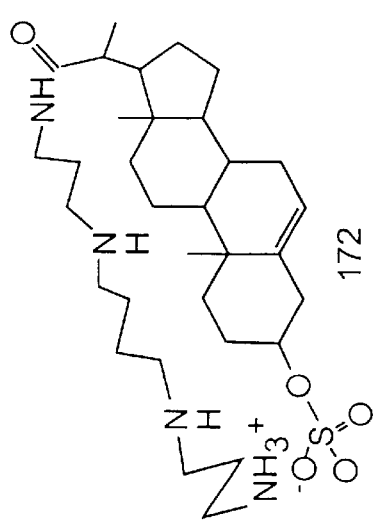

The structure of GL-172 is known. (Deng, JACS 1996, 118, 8975–8976). GL-172, along with other representative small molecule ionophores, are depicted in FIG. 1. Additional small molecule ionophores useful in the practice of the invention have the structure:

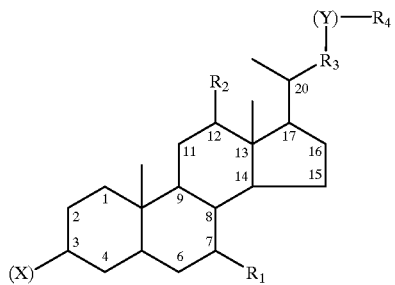

wherein:

($R_1$) is H or OH;

($R^2$) is H or OH, wherein ($R_1$) and ($R_2$) are the same or different;

($R_3$) is a saturated or unsaturated alkyl chain which is branched or unbranched, wherein a preferred embodiment, ($R_3$) is a $(CH_x)_m$ group wherein x=0, 1, or 2 and m=from 0 to 10;

(X) is $SO_4^-$, $PO_4^{2-}$, $HOPO_3^-$, or $CO_2^-$;

(Y) is a linking group or is absent; and ($R_4$) is an amine, alkylamine, or polyalkylamine.

The linking group (Y) connects the amine ($R_4$) to the cholesterol derivative. Examples of (Y) groups include $<C=O$; $—CH_2—O—C(=O)—$; $—O—C(=O)—$; $—CH_2—NH—$; $—C(=O)—NH—$; and $—NH—C(=O)—O—$. The orientation of the linking group is not significant. Additional linking groups that may be useful in the practice of the invention are groups that contain no more than three or four atoms and form a bridge of covalent bonds between ($R_4$) and the cholesterol derivative. Examples would include $—(CH_2)_2—$; $—(CH_2)_3—$; $—(CH_2)—(C=O)—$; $—(CH_2)_n—NH—(C=O)—$ where n is preferably 4 or less; or small amino acids such as glycinyl, alanyl, beta-alanyl, serinyl, and the like.

($R_4$) represents an amine structure (including primary and secondary and tertiary amines) which can vary in both the number of nitrogen atoms and the number of carbon atoms separating each nitrogen. These structures are known in the art as amines, alkylamines, or polyalkylamines. The amine, alkylamine or polyalkylamine may be attached to the linker (Y) (or directly to the steroid if the linker is absent) at any carbon or nitrogen atom in the alkylamine or polyalkylamine chain.

The alkylamine or polyalkylamine groups as defined herein may include one or more carbon-carbon double bonds and the use of such alkenylamines is therefore within the practice of the invention. Since the alkylamine or polyalkylamine groups may be saturated or unsaturated the term "alkylamine" encompasses alkenylamines in the description of the invention. The alkylamines and polyalkylamines may also be branched or unbranched. A branched alkylamine or polyalkylamine would comprise an alkyl, alkylamine, or polyalkylamine chain that was connected to any carbon or nitrogen atom of the primary alkylamine or polyalkylamine chain. The primary alkylamine or polyalkylamine chain would then be attached to the linker (Y) (or directly to the steroid if the linker was absent).

In a preferred embodiment of the invention ($R_4$) is spermine or spemidine. The spermine or spermidine is attached to the linker (Y) (or directly to the steroid if the linker was absent) by any carbon or nitrogen atom of the spermine or spermidine group.

Representative alkylamines include:
(a) $NH_2—(CH_2)_z—$;
(b) $NH_3^+—(CH_2)_z—$;
(c) $CH_3—(CH_2)_z—N[—CH_2—CH_3]—$ (attached to (Y) by the N atom);
(d) $[CH_3(CH_2)_y]NH—(CH_2)_z—$; and
(e) $[[CH_3—(CH_2)_x][CH_3—(CH_2)_y]]—N—(CH_2)_z—$;

where x, y and z are from 1 to 10.

Representative polyalkylamines include:
(a) $—[NH—(CH_2)_x]_m—NH_3^+$;
(b) $H—[NH—(CH_2)_y]_p—[NH—(CH_2)_z]_q—$;
(c) $—[NH—(CH_2)_x]_m—[NH—(CH_2)_y]_n—[NH—(CH_2)_z]_p—NH_3^+$;
(e) $H—[NH—(CH_2)_x]_n—N—CH_2—[NH—(CH_2)_y]_p—[NH(CH_2)_z—]_q—NH_3^+$, (attached to (Y) by a N atom in the middle of the chain);
(d) $H—[NH—(CH_2)_w]_m—[NH—(CH_2)_x]_n—[NH—(CH_2)_y]_p—(NH—(CH_2)_z]_q—$;
(e) $H—[NH—(CH_2)_w]_m—[NH—(CH_2)_x]_n—N—[[CH_3(CH_2)_y]N]—(CH_2)_z—NH_3^+$; and
(f) $NH_3^+—[CH[(CH_2)_x—NH_3^+]—CH_2]—CH—[NH—(CH_2)_w]_m—NH_3^+$, (attached to (Y) by the carbon atom in the middle of the chain);

where m, n, p, q, w, x, y and z are from 1 to 10.

Any combination of alternating amine and alkyl moieties creates an ($R_4$) structure within the scope of the invention. Additionally, this alternating combination of amine and alkylamine moieties may be attached to the linker (Y) or directly to the steroid by any carbon or nitrogen atom in the ($R_4$) group.

Small molecule ionophores according to the practice of the invention may also include a variety of structures as the steroid group:

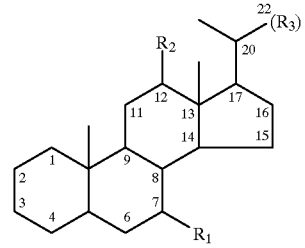

In a preferred embodiment, as shown above, the steroid group is linked to (Y) (or directly to ($R_4$) if (Y) is absent) from ring position 17 of the steroid nucleus or from the arm that normally extends from position 17 in many steroids (for example, position 20 and 22), or from any lengthened, shortened, branched or unbranched form of said arm ($R_3$). In this embodiment, the steroid group is attached to (X) at position 3 of the steroid nucleus. The orientation of the steroid group, that is, how the steroid is attached (with or without a linker (Y)) to the (X) and ($R_4$) groups, can be quite varied. Any ring position or substituent on the steroid can in general be used as a point of attachment. For example, in another preferred embodiment, the steroid group is linked to (Y) (or directly to ($R_4$) if (Y) is absent) from ring position 3 of the steroid nucleus and the steroid group is attached to (X) at position 17 or from the arm that normally extends from position 17 (for example, position 20 and 22), or from any lengthened, shortened, branched or unbranched form of said arm ($R_3$) as follows:

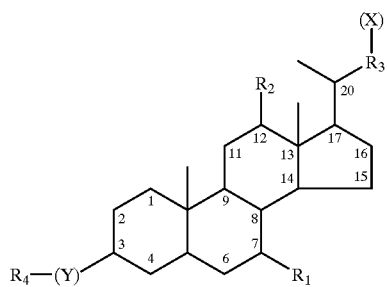

In a further embodiment of the invention, the steroid may contain various degrees of unsaturation. That is, double bonds may exist at numerous positions within the steroid nucleus. For example, a double bond may be present between position 5 and 6, or 7 and 8, or between 5 and 6, and 7 and 8 as follows:

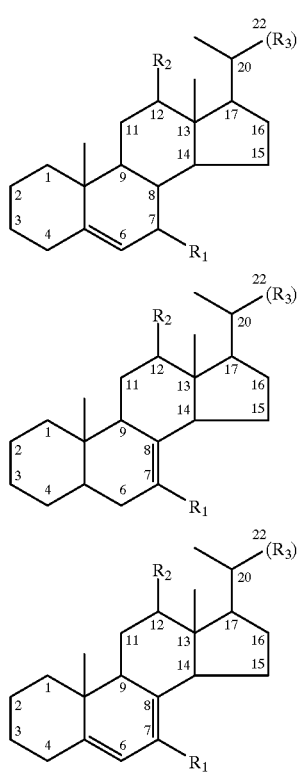

A further group of ionophores useful in the practice of the invention have the structure:

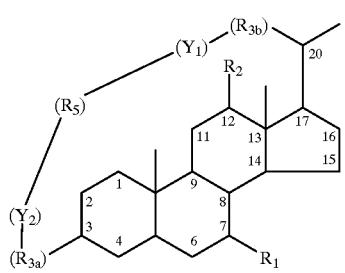

wherein:
 ($R_1$) is H or OH;
 ($R_2$) is H or OH, wherein ($R_1$) and ($R_2$) are the same or different; ($R_{3a}$) and ($R_{3b}$) are each a saturated or unsaturated alkyl chain which is branched or unbranched, wherein a preferred embodiment of ($R_{3a}$) or ($R_{3b}$) is a $(CH_x)_m$ group wherein x=0, 1, or 2 and m=from 0 to 10. ($R_{3a}$) and ($R_{3b}$) may be the same or different;
 ($Y_1$) and ($Y_2$) are linking groups or are absent (none, either, or both may be absent); and
 ($R_5$) is an alkylamine or polyalkylamine.

The linking groups ($Y_1$) and (Y2) connect the amine ($R_5$) to the cholesterol derivative. Examples of ($Y_1$) and ($Y_2$) and additional ($Y_1$) and ($Y_2$) groups that may be useful in the practice of the invention are the same as those previously described for the linking group (Y). ($Y_1$) and ($Y_2$) may be the same or different. Additionally, one may be absent while the other is present, neither may be absent, or both may be absent.

($R_5$) represents an amine structure (including primary and secondary and tertiary amines) which can vary in both the number of nitrogen atoms and the number of carbon atoms separating each nitrogen. ($R_5$) differs from the previously described alkylamine and polyalkylamine structures because of the existence of two points of attachment to the steroid group. The alkylamine or polyalkylamine is attached to the steroid (with or without a linker bond) at two different positions of the steroid nucleus. The alkylamine or polyalkylamine may be attached to a linker (or directly to the steroid if the linker is absent) at any carbon or nitrogen atom in the alkylamine or polyalkylamine chain. Additionally, any ring position or substituent on the steroid can in general be used as a point of attachment to the steroid nucleus.

The alkylamine or polyalkylamine groups as defined herein may include one or more carbon-carbon double bonds and the use of such alkenylamines is therefore within the practice of the invention. Since the alkylamine or polyalkylamine groups may be saturated or unsaturated the term "alkylamine" encompasses alkenylamines in the description of the invention. The alkylamines and polyalkylamines may also be branched or unbranched. A branched alkylamine or polyalkylamine would comprise an alkyl, alkylamine, or polyalkylamine chain that was connected to any carbon or nitrogen atom of the primary alkylamine or polyalkylamine chain. The primary alkylamine or polyalkylamine chain would then be attached to the linkers ($Y_1$ and $Y_2$) (or directly to the steroid if either linker were absent).

In a preferred embodiment of the invention ($R_5$) is spermine or spemidine. The spermine or spermidine is attached to each of the linkers (or directly to the steroid if either linker is absent) by a carbon or nitrogen atom near each end of the spermine or spermidine group. Representative alkylamines and polyalkylamines were presented in a description of ($R_4$). It would be straightforward for one of ordinary skill in the art to attach the amine moieties of ($R_4$) at two different carbon or nitrogen atoms in the alkylamine or polyalkylamine chain in order to use the moieties for ($R_5$).

Any combination of alternating amine and alkyl moieties creates an ($R_5$) structure within the scope of the invention. Additionally, this alternating combination of amine and alkylamine moieties may be attached to the linkers ($Y_1$ and $Y_2$) or directly to the steroid by any two carbon or nitrogen atoms in the ($R_5$) group. The minimum and maximum length of the amine moiety is of course restricted by the two points of attachment between the amine moiety and the steroid nucleus.

According to the practice of the invention, this embodiment may also include a variety of structures as the steroid group. In a preferred embodiment, as shown above, the steroid group is linked to $(Y_1)$ and $(Y_2)$ (or directly to $(R_5)$ if either or both (Y) is absent) from ring position 17 of the steroid nucleus or from the arm that normally extends from position 17 in many steroids (for example, position 20 and 22), or from any lengthened, shortened, branched or unbranched form of said arm, and from ring position 3 of the steroid nucleus. The orientation of the steroid group, that is, how the steroid is attached (with or without linkers ($Y_1$ and $Y_2$)) to the two positions on the $(R_5)$ group, can be quite varied. Any ring position or substituent on the steroid can in general be used as a point of attachment.

In a further embodiment of the invention, the steroid may contain various degrees of unsaturation. That is, double bonds may exist at numerous positions within the steroid nucleus as described for the previous embodiments.

Additionally, a third group of ionophores useful in the practice of the invention are described as membrane spanning structures. Not to be limited as to theory, membrane spanning structures are believed to form a membrane spanning ion channel. The transmembrane channel formed across the bilayer would selectively allow ions to flow through the channel and across the bilayer.

In a preferred embodiment of the invention, the membrane spanning compounds are of a di-steroid form. Di-steroid compounds useful in the practice of the invention include:

group wherein x=0, 1, or 2 and m=from 0 to 10. $(R_{3c})$ connects the two steroid groups (through linker groups $(Y_1)$ and $(Y_2)$ if present) to one or two amine groups, $(R_4)$ or $(R_{4a})$ and $(R_{4b})$ (through linker groups $(Y_3)$ and $(Y_4)$ if present). Preferred embodiments of $(R_{3c})$ include:

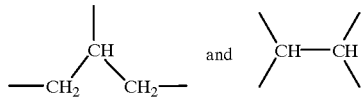

$(Y_1)$, $(Y_2)$, $(Y_3)$ and $(Y_4)$ are linking groups or are absent (none, any, or all may be absent); and $(R_4)$ is an alkylamine or polyalkylamine.

The linking groups $(Y_1)$, $(Y_2)$, $(Y_3)$ and $(Y_4)$ connect the amines $(R_4)$ or $(R_{4a})$ and $(R_{4b})$ to the di-cholesterol derivative compound. Examples of $(Y_1)$, $(Y_2)$, $(Y_3)$ and $(Y_4)$ and additional $(Y_1)$, $(Y_2)$, $(Y_3)$ and $(Y_4)$ groups that may be useful in the practice of the invention are the same as those previously described for the linking group (Y). $(Y_1)$, $(Y_2)$, $(Y_3)$ and $(Y_4)$ may be the same or different. Additionally, any may be absent, none may be absent, or all may be absent.

$(R_4)$ or $(R_{4a})$ and $(R_{4b})$ represents an amine structure (including primary and secondary and tertiary amines) which can vary in the both the number of nitrogen atoms and the number of carbon atoms separating each nitrogen. Pre-

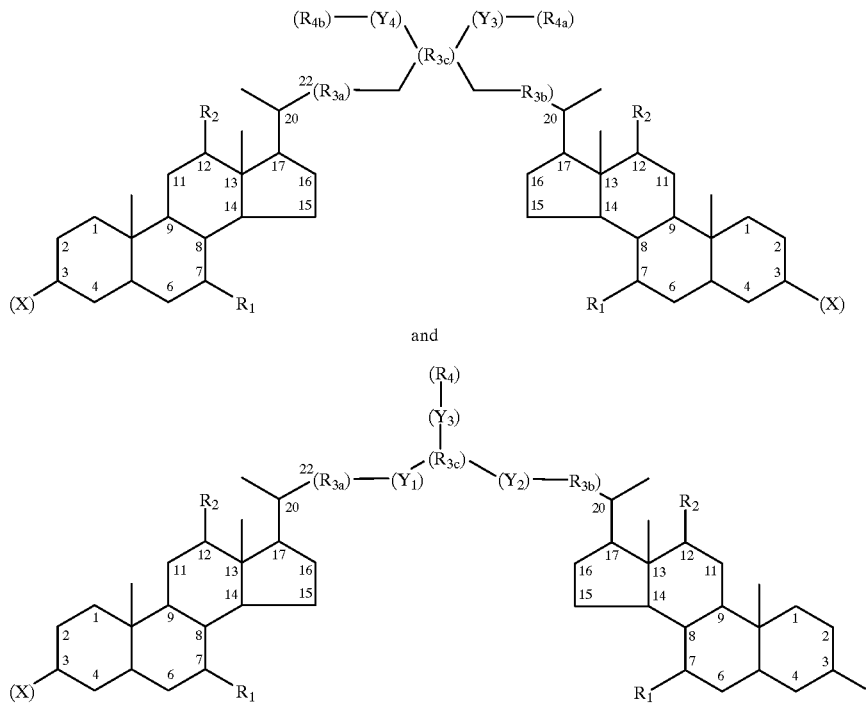

wherein:

(X) is $SO_4^-$, $PO_4^{2-}$, $HOPO_3^-$, or $CO_2^-$;

$(R_1)$ is H or OH;

$(R_2)$ is H or OH, wherein $(R_1)$ and $(R_2)$ are the same or different; $(R_3)$(a, b, and c) are saturated or unsaturated alkyl chains which are branched or unbranched. A preferred embodiment of $(R_{3a})$ and $(R_{3b})$ is a $(CH_x)_m$ ferred amine, alkylamine, and polyalkylamine structures for $R_4$ (including $(R_{4a})$ and $(R_{4b})$) are disclosed above.

According to the practice of the invention, this embodiment may also include a variety of structures as the steroid group. In a preferred embodiment, as shown above, the steroid groups are linked to one another from ring position 17 of the steroid nucleus or from the arm that normally extends from position 17 in many steroids (for example, position 20 and 22), or from any lengthened, shortened, branched or unbranched form of said arm (through (Y) and (R) groups, if present, as shown above). The steroid groups may also be linked from ring position 3 of the steroid nucleus using similar moieties as above. The orientation of the steroid groups, that is, how the steroids are attached (with or without (Y's) and ($R_3$'s)) to one another, to the ($R_4$) group or groups, and to (X) can be quite varied. Any ring position or substituent on the steroid can in general be used as a point of attachment.

In a further embodiment of the invention, the steroid may contain various degrees of unsaturation. That is, double bonds may exist at numerous positions within the steroid nucleus as described for a previous embodiment.

A still additional embodiment of the di-steroid type structures is a group of compounds with an (X) group connecting the steroid moieties as follows:

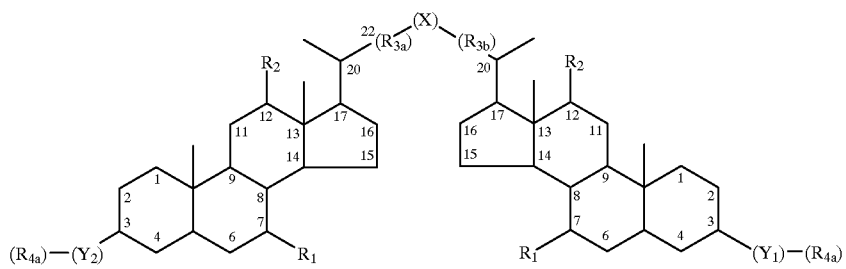

wherein the substituents as are defined above for other di-steroid compounds.

An additional preferred embodiment for (X) of the di-steroid compounds is

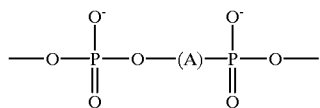

wherein (A) is —$(CH_2)_m$—O— with m=2 to 10. or (A) is absent.

The invention provides also for pharmaceutical compositions of ionophores as the free compound, or as a pharmaceutically acceptable salt thereof. Additionally the ionophores of the present invention may be the active ingredient in a pharmaceutical composition that includes carriers, fillers, extenders, dispersants, creams, gels, solutions and other excipients that are common in the pharmaceutical formulatory arts.

In a further aspect, the invention provides methods of administering the ionophores and the pharmaceutical compositions of the present invention by intravenous, oral, instillation, inhalation, topical, intraperitoneal, subcutaneous, transmucosally, or intramuscular routes The ionophores and the pharmaceutical compositions may be administered, for example, in the form of capsules, powders, tablets, liquids, solutions, and aerosolized solutions. Furthermore, nebulizing devices, powder inhalers, injection into the body cavity of the patient, sustained-release formulation, delivery using additional micelles, gels, or liposomes, and intravenous injection are representative methods of administration.

In a preferred embodiment, the ionophore can be directly administered orally to airway epithelia to treat the Cl⁻ and fluid transport which is effected by CF.

Another important embodiment of the invention is the use of the antibiotic activity of the ionophores in combination with the introduction of artificial Cl⁻ channels. The defective fluid transport in airway epithelia leads to recurring bacterial infections in the lungs of a CF patient. The known antibiotic activity of the squalamine mimics can be used to treat the infections while providing artificial chloride channels and improving chloride secretion.

Dosages of the compositions will vary, depending on factors such as half-life of the ionophore, potential adverse effects of the ionophore or of degradation products thereof, the route of administration, the condition of the patient, and the like. Such factors are capable of determination by those skilled in the art. The exact dose levels given on a daily basis, of course, is meant to be adapted by the physician to provide the optimum therapeutic response.

EXAMPLES

Example 1

Synthesis of Ionophores

GL-172

Figure 2:
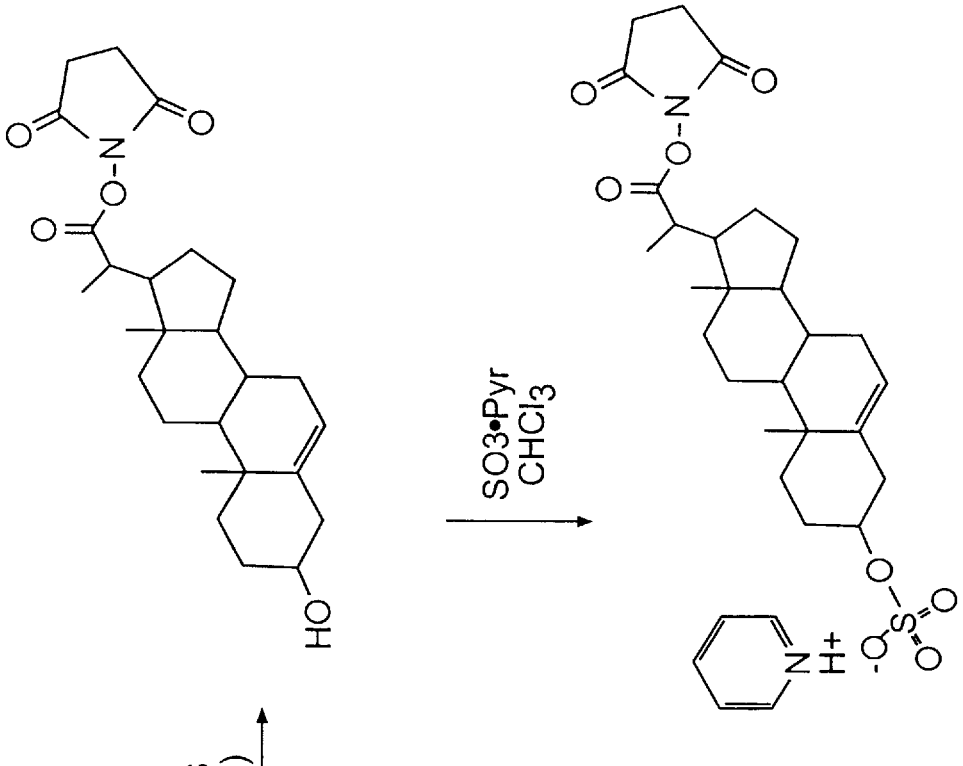
FIG. 2. depicts a synthetic pathway of a small molecule ionophore.
Figure 2:
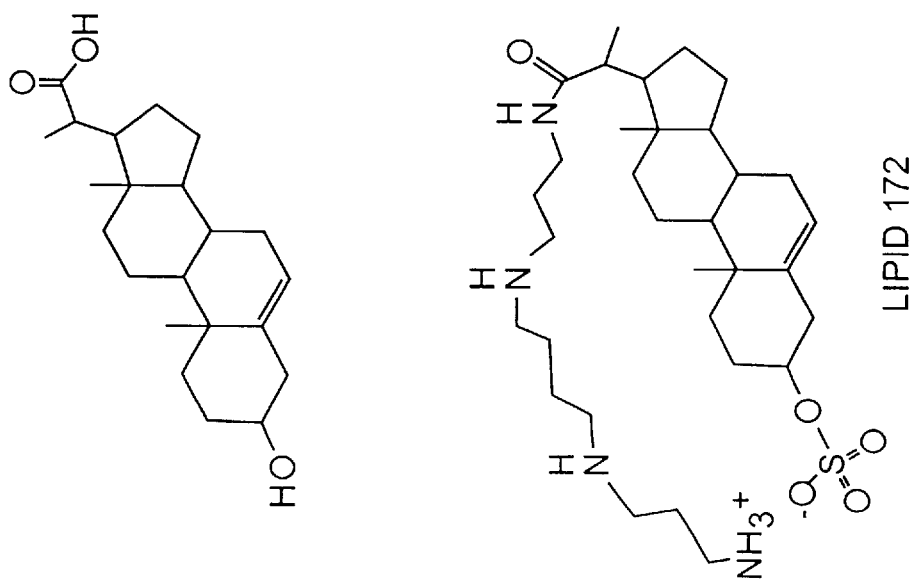

A scheme for the synthesis of GL-172 is shown in FIG. 2. 5-Cholenicacid-22, 23-bisnor-36-ol (487 mg, 1.41 mmol) was suspended in THF (50 mL) and N-hydroxysuccinimde (178 mg, 1.55 mol) and DCC (437 mg, 2.12 mmol) were added. The reaction was stirred for three hours in a 50° C. oil-bath. The reaction was filtered and a basic (sodium bicarbonate) work-up was performed. The resulting crude (1.09 g) was dry-loaded (10 g silica) onto a silica gel column (95 g) and was eluted with 50% ethyl acetate/hexanes. The desired material was isolated and characterized by ¹HNMR as the hydroxybisnorcholenic acid-NHS-ester (571 mg, 92%).

The hydroxybisnorcholenic acid-NHS-ester (460 mg, 1.04 mmol) was dissolved in chloroform (50 mL) and sulfur trioxide pyridine complex (499 mg, 3.14 mmol) was added. The reaction was stirred for 4 hours then an aqueous work-up was performed. The crude material (570 mg) was taken on without purification.

A suspension of the sulfonate (50 mg, 0.583 mmol) in DMF was added to a solution of spermine (189 mg, 0.934 mg) in DMF (17.5 mL) and the reaction was stirred for 1.5 hours. The solvent was removed and the resulting crude was purified by flash column chromatography (50 g silica gel) eluting with a gradient of 40:25:2, 40:25:5, and 40:25:10. The desired material was isolated and characterized by ¹HNMR as hydroxybisnorcholenic-spermine-sulfonate, Lipid 172 (140 mg, 38%).

Analog of GL-172

Synthesis of hydroxybisnorcholenicmethylester-imidazole formate. Hydroxybisnorcholenic acid (498 mg, 1.45 mmol) was suspended in 1:1 chloroform/methanol (100 ml) and concentrated sulfuric acid (5.0 ml). The reaction was refluxed for 6 hours and an aqueous work-up was performed. The resulting crude material was purified by flash column chromatography (50 g silica gel) eluting with 50% ethyl acetate/hexanes. The desired material was isolated and characterized by 1HNMR as the hydroxybisnorcholenicacid-methyl ester (307 mg, 59%).

The hydroxybisnorcholenic acid methyl ester (315 mg, 0.879 mmol) was dissolved in methylene chloride (50 ml and Hunig's base (0.15 ml, 0.879 mmol) was added followed by phosgene (1.93 M in toluene, 2.28 ml, 4.395 mmol). After stirring the reaction overnight a solution of imidazole (658 mg, 9.67 mmol) in methylene chloride (50 ml) was added. The reaction was again stirred overnight and an aqueous work-up was performed. The crude material was purified by flash column chromatography (40 g silica gel) eluting with 30% ethyl acetate/hexanes. The desired material was isolated and characterized by $^1$HNMR as the bisnorcholenicacid-methylester-immidazoleformate (336 mg, 92%).

The methylester-imidazole formate (330 mg, 0.729 mmol) in methylene chloride (25 ml) was added to a solution of spermine (369 mg, 1.83 mmol) and DMAP (15 mg) in methylene chloride (25 ml) and the reaction was stirred for two days. An aqueous work up was performed and the resulting crude was purified by flash column chromatography (35 g silica gel) eluting with a gradient of 4:25:2, 40:25:5, and 40:25:10 chloroform/methanol/ammonium hydroxide. The desired materials were isolated and characterized by $^1$HNMR as the bisnorcholenicacid-methylester-sperminecarbamate (170 mg, 40%), Lipid 182.

Example 2

Cell Membrane Halide Permeability Assessed by SPQ

The tracheobronchial surface epithelial cell line (CFT1) was generated from a CF (ΔF 508) patient and characterized by Dr. Yankaskas et al. at the University of North Carolina at Chapel Hill. The cells were cultured as described previously. (Yankaskas et al., *Am. J. Physiol.*, 264, C1219–1230 (1993)) Briefly, CFT1 cells were seeded onto 12-well cell culture plates at a density of 50,000 cells/cm$^2$ and cultured with Ham's F12 medium supplemented with 2% fetal bovine serum, 5 μg/ml insulin, 3.7 μg/ml endothelial cell growth supplement, 25 ng/ml epidermal growth factor, 30 nM triiodothyronine, 1 μM hydrocortisone, 5 μg/ml transferrin, and 10 ng/ml cholera toxin (Gibco).

Cl$^-$ channel activity was assessed with the halide-sensitive fluorophore, 6-methoxy-N-(3-sulfopropyl)-quinolinium (SPQ), as reported previously (Marshall et al., *J.Biol.Chem.* (1994); Jiang et al., *Am.J.Phsiol.*, 275 (Cell Physiol.44):C, (1998)). SPQ fluorescence was initially quenched by incubating the cell up to 30 minutes in a NaI buffer of the following composition (mM): 135 NaI, 2.4 K$_2$HPO$_4$, 0.6 KH$_2$PO$_4$, 1 MgSO$_4$, 1 CaSO$_4$, and 10 N-2-hydroxyethylpiperazine-n'-2-ethanesulfonic acid, pH=7.4. After measuring baseline fluorescence (Fo) for 2 minutes, the NaI solution was replaced with a solution in which NaI was substituted by NaNO$_3$. Five minutes later, a cocktail of forskolin (20 μM) and IBMX (100 μM) was added to stimulate the CFTR Cl$^-$ channel activity.

An increase in halide permeability is reflected by a more rapid increase in SPQ fluorescence. It is the rate of change rather than the absolute change in signal that is the important variable in evaluating anion permeability. Differences in absolute levels reflect quantitative differences between groups in SPQ loading, size of cells, or number of cells studied. The data are presented as means±SE of fluorescence at time t (Ft) minus the baseline fluorescence (Fo, the average fluorescence measured in the presence of I$^-$ for 2 min before ion substitution) and are representative of results obtained under each condition. For each experiment, between 50 to 100 cells were examined on a given day and studies under each condition were repeated on at least two days. For each experiment, the responses were compared with those obtained with control or untreated cells. Cells were scored as positive if they exhibited a rate of change in fluorescence that was greater than the signal observed with the control cells. Under the conditions specified above, control cells were unresponsive to added cAMP agonists. There was a broad spectrum in the rate of change in SPQ fluorescence observed with responsive cells. Normally, we scored cells as responsive if the slope of the response curve, which is indicative of the rate of increase in SPQ fluorescence, was ≧0.364 following stimulation with cAMP agonists. Because the response was heterogenous, the data shown are for the 10% of cells in each experiment showing the greatest response. All the field were evaluated but for clarity of presentation, only top 10% of responders are illustrated in the figures.

CFT1 cells retain the bioelectrical characteristics of primary human CF airway epithelial cells, however, CFTR Cl$^-$ channel activity is defective. Forskolin (10 μM) and IBMX (100 μM) only cause a small increase in SPQ fluorescence in less than 1% of the CFT1 cells. In this study, DMSO (0.5%, v/v), the solvent of GL-172, did not cause an increase in SPQ fluorescence. By contrast, in more than 10% of the CFT1 cells, GL-172 (100 μM, dissolved in DMSO) induced a significant increase in SPQ fluorescence (FIG. 2), indicating an increased anion permeability.

CF airway epithelial (CFT1) cells were loaded with SPQ. NO$_3^-$ was substituted for I$^-$ in the bathing solution at 0 min. GL-172 (100 μM, dissolved in DMSO; squares) or equal volume of DMSO (0.5%, v/v; circles) was added into the bathing solution 6 min after ion substitution (arrow). Data are presented in FIG. 2 as mean±SEM of fluorescence at the time (F$_t$) minus the baseline fluorescence (F$_0$, average fluorescence measured before ion substitution for 2 min).

Example 3

Cl$^-$ Permeability Assessed by I$_{sc}$ Measurement

Primary human tracheobronchial epithelial (NHBE) cells were purchased from Clonetics Corporation (San Diego, Calif.). NHBE cells were passaged once and then seeded directly onto collagen-coated semi-permeable inserts (Millicell-PCF, 0.4 mm pore size, 0.6 cm$^2$ growth area) at a density of approximately 5×10$^5$ cells/cm$^2$ and grown at the air-liquid interface (Jiang et al., *Science* 262, 424–427 (1993); Jiang et al., *Human Gene Therapy*, 9:(July 20) (1998)). A mixture (1:1) of Dulbecco's modified Eagle's medium (DMEM) and Bronchial Epithelial Growth Medium (BEBM) supplemented with growth factors and antimicrobials supplied as BEGM Bulletkit (Clonetics Corporation), was changed every other day. Transepithelial resistance (R$_1$) was monitored every other day starting at day 3 using an ohmmeter. Fisher rat thyroid epithelial (FRT) cells (Zurzolo et al., *J. Cell Biol.*, 121:1031–1039 (1993)) were cultured as NHBE cells except that the culture medium was DMEM supplemented with 5% fetal bovine serum (Sigma).

Polarized airway epithelial cells were mounted in modified Ussing chambers (Jim's Instruments, Iowa City, Iowa)

interfaced with electrodes and bathed bilaterally in Krebs-Ringers solution (135 mM NaCl, 2.4 mM $K_2HPO_4$, 0.6 mM $KH_2PO_2$, 1.2 mM $CaCl_2$, 1.2 mM $MgCl_2$, 25 mM $NaHCO_3$, and 10 mM glucose, pH 7.4) bubbled with 95% $O_2$ and 5% $CO_2$ (Rich et al., *Hum. Gene Ther.* 4:461–476, (1993); Zabner et al, *J. Biol. Chem.* 270, 18997–19007 (1994); Jiang et al., *Am.J.Physiol.* 271, L527–537 (1996). On the mucosal side, NaCl was replaced with 135 mM sodium gluconate to create a transepithelial $Cl^-$ concentration gradient. Transepithelial voltage was measured for 5 min after which it was clamped to 0 mV and changes in short circuit current ($I_{sc}$) determined. After a stable base line was achieved, the cells were treated sequentially with 100 μM amiloride (to estimate the amiloride-sensitive $Na^+$ channel), a cocktail containing 10 μM forskolin and 100 μM 3-isobutyl-1-methyl-xanthine (IBMX) (to stimulate transepithelial $Cl^-$ current through the CFTR $Cl^-$ channels) and 10 to 100 μM 5-nitro-2(3-phenylpropylamino)benzoate (NPPB, a $Cl^-$ channel blocker to inhibit CFTR $Cl^-$ channels) (Hasegawa et al., *Science* 258, 1477–1479 (1992)). Amiloride and NPPB were added to the mucosal solutions while the forskolin and IBMX mix were added to the submucosal solutions.

Effects of GL-172 on Cl– permeability assessed by $I_{sc}$ measurement

Figure 3:
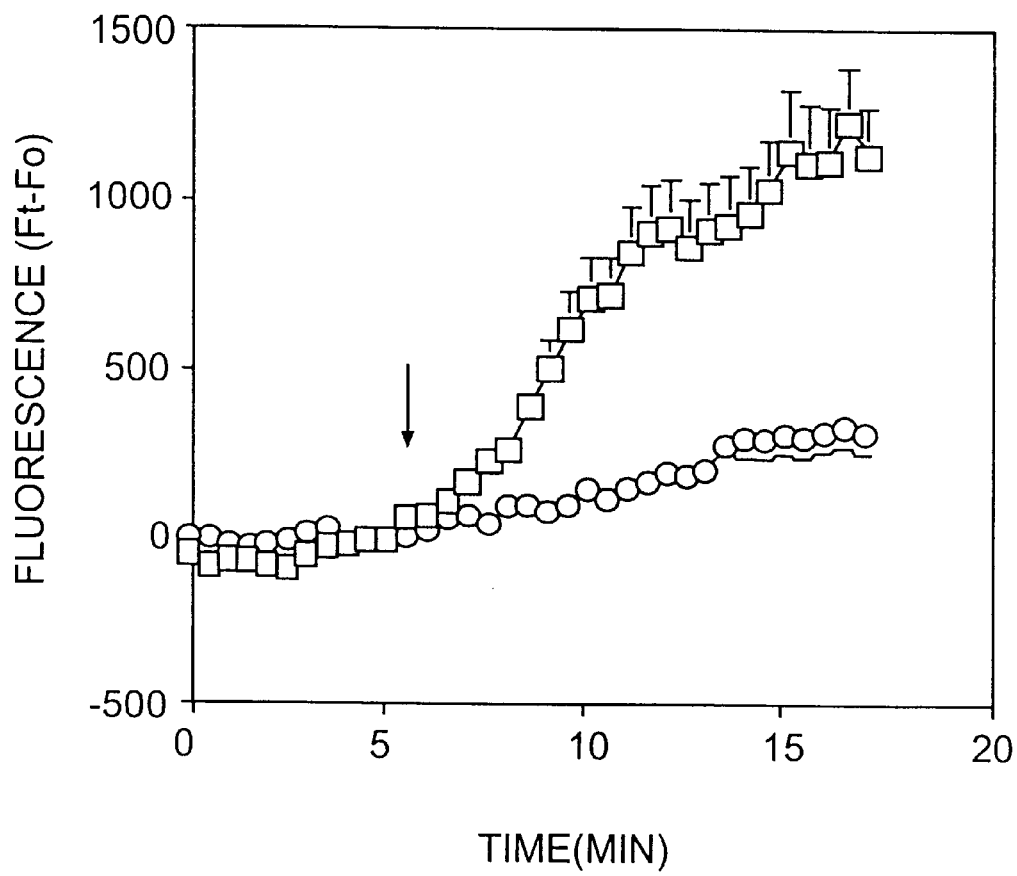
FIG. 3. depicts GL-172 induced increase in anion permeability, determined by SPQ analysis.

Polarized NHBE cells that had developed a $R_1$ of $\geq 1000$ $\Omega \cdot cm^2$ were mounted between two halves of a modified Ussing chamber for $I_{sc}$ measurement. FIG. 3a shows that addition of amiloride (100 μM) into the apical side caused a decrease in $I_{sc}$, indicating the presence of an amiloride-sensitive $Na^+$ conductance. In the continuous presence of amiloride, a cocktail, of forskolin (10 μM) and IBMX (100 μM) induced a significant increase in $I_{sc}$. This increase in $I_{sc}$ represents the maximum $Cl^-$ conductance through cAMP-mediated channels under these experimental conditions since the cocktail of forskolin and IBMX stimulates the maximum increase in intracellular CAMP. Data from six independent experiments showed that an average increase in $I_{sc}$ of $11.3 \pm 1.6$ μA/cm² (mean±SEM) was generated by the cocktail. To further ascertain that the increase in $I_{sc}$ is mediated by cAMP-mediated Cl channels, NPPB (100 μM) was used to inhibit the response.

Figure 4:
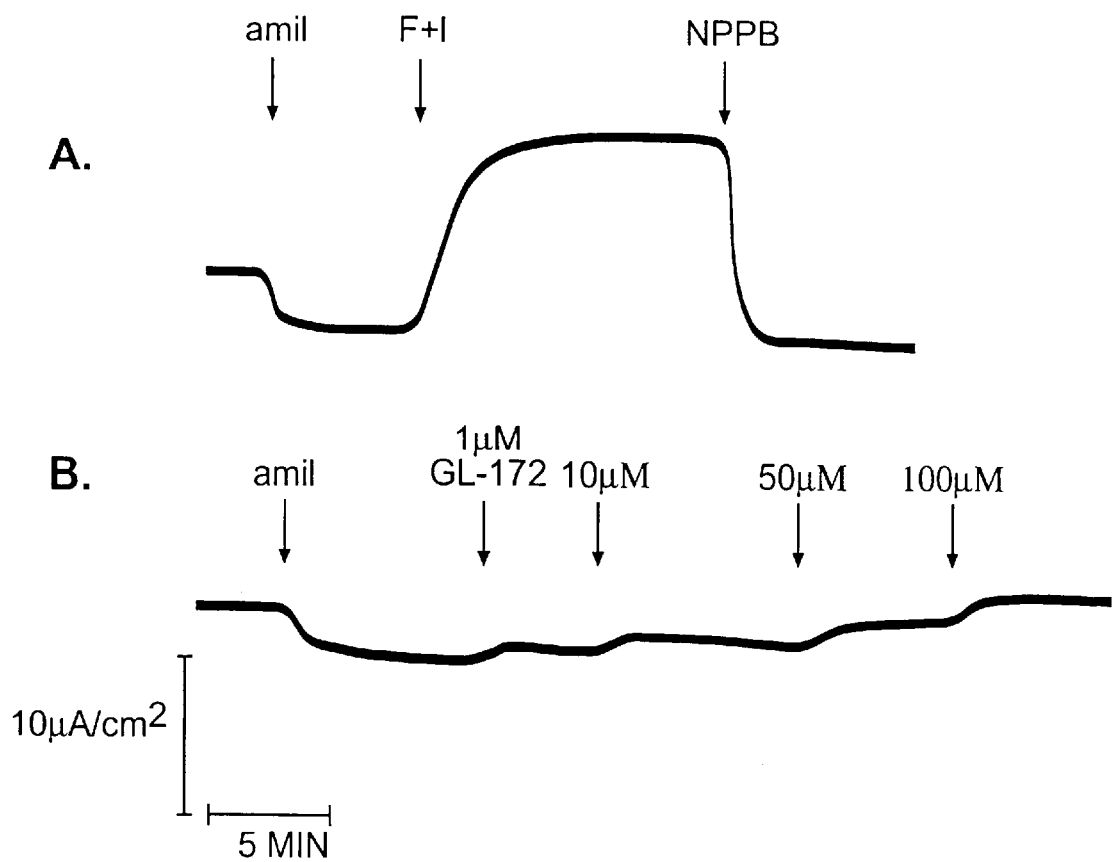
FIG. 4. depicts representative tracings of GL-172 induced ($\Delta I_{sc}$) in human tracheobronchial epithelial (NHBE) cells. After addition of 10 $\mu$M amiloride, a cocktail of 10 $\mu$M forskolin and 100 $\mu$M IBMX (A) or GL-172 (B) at different accumulative concentrations was added to the apical side of the polarized epithelia.

The increase in $I_{sc}$ in response to GL-172 is shown in FIG. 3B. GL-172 was dissolved in DMSO and added into the apical side in an accumulative fashion. In the presence of amiloride (100 μM), GL-172 stimulated a dose-dependent increase in $I_{sc}$. The response was rapid and sustained, similar to that stimulated by forskolin and IBMX. DMSO, up to two times of the volume/volume concentration as the solvent for GL-172, did not cause any significant increase in $I_{sc}$. Data from 5 independent experiments are summarized in FIG. 4. Statistical analysis suggest that the increase in $I_{sc}$ induced by GL-172 is significant (p<0.01). The increase in $I_{sc}$ induced by GL-172 at concentrations of 10 and 100 μM were about 20% and 35% of the maximum response stimulated by the cocktail of forskolin and IBMX.

Experiments were also performed in FRT cells which had no cAMP-mediated response. GL-172 caused a similar response in FRT cells. These results suggest that the increase in $I_{sc}$ induced by GL-172 in NHBE cells were independent of CFTR $Cl^-$ channels or other cAMP-mediated $Cl^-$ channels.

Example 4

Effects of Ionophores on the Nasal Epithelium of Transgenic CF Mice

Nasal potential difference (PD) measurements in transgenic CF mice

The FABP-CFTR bitransgenic (Zhou et al., *Science* 266, 1705–1708 (1995)) mice were obtained from Jackson Laboratories. Some of the animals used in these studies were bred at Genzyme Corporation. The PD across the nasal epithelium of the CF mice was measured as described previously (Grubb et al., *Nature* 371, 802–806, (1994); Zeiher et al., *J. Clin. Invest.* 96, 2051–2064 (1995); Jiang et al., *Human Gene Therapy*, 8:671–680 (1997); Jiang et al., *Human Gene Therapy*, 9:(July 20) (1998)). Briefly, a 23-gauge subcutaneous needle filled with Ringer solution (135 mM NaCl, 2.4 mM $K_2HPO_4$, 0.6 mM $KH_2PO_4$, 1.2 mM $CaCl_2$, 1.2 mM $MgCl_2$, and 10 mM Hepes, pH 7.4) was used as a reference electrode. The exploring electrode (pulled from PE-20 tubing and filled with Ringer solution) was inserted approximately 5 mm into the nasal cavity. The electrodes were electrically coupled by agar bridges (3% agar, 1 M KCl) that were inserted into the fluid stream of the flowing bridges and connected by calomel electrodes to a digital voltmeter (Iso-millivoltmeter; World Precision Instruments). Signals were recorded using a strip chart recorder (Servocoder model 6221).

Following placement of the electrodes, the nasal passage was perfused with Ringer solution through a separate catheter at 5–20 μl/min for 3 to 5 min using a micropump (model 55-3206; Harvard Apparatus). Once a baseline was achieved, the perfusing solution was switched to Ringer solution containing 100 μM amiloride and perfusion continued until a new steady state was reached. The perfusing solution was then replaced with a low $Cl^-$ Ringer solution (NaCl was replaced by NaGluconate) containing GL-172 or DMSO in the presence of amiloride.

Data are expressed as mean±SEM. The number of animals examined or individual experiments performed is indicated by "n". Statistical analysis was performed using ANOVA followed by Student-Newman-Keuls test. In experiments involving only two groups, unpaired Student's t test was used to compare the means. A p value of less than 0.05 was considered statistically significant.

Effects of GL-172 on the nasal epithelium of transgenic CF mice

The nasal mucosae of transgenic CF mice have been used previously to evaluate the ability of adenovirus and cationic lipid/DNA gene delivery vectors to restore the epithelial $Na^+$ and $Cl^-$ transport defects in these animals (Grubb et al., *Nature* 371, 802–806, (1994); Zeiher et al., *J. Clin. Invest.* 96, 2051–2064 (1995); Jiang et al., *Human Gene Therapy*, 8:671–680 (1997); Jiang et al., *Human Gene Therapy*, 9:(July 20) (1998)). Because the utility of CF null (−/−) mice can be limited by intestinal complications (Snouwaert et al., *Science* 257, 1083–1088 (1992)), we used the FABP-CFTR (−/−) bitransgenic mice (Zhou et al., *Science* 266, 1705–1708 (1994)). The nasal epithelium of the FABP-CFTR bitransgenic (−/−) mice manifested the electrophysiological abnormalities observed in CF null (−/−) animals and human subjects with CF.

Figure 5:
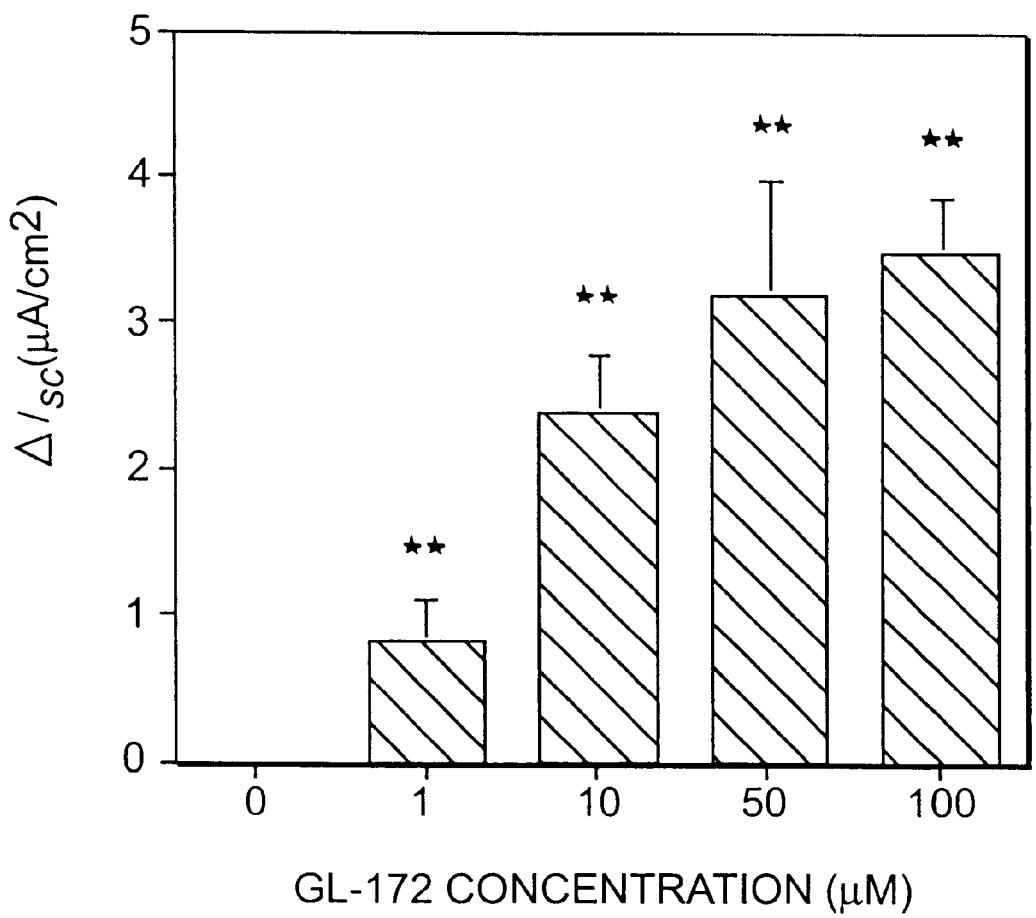
FIG. 5. Summary of GL-172 induced changes in short circuit current ($\Delta I_{sc}$) in airway epithelial cells.
Figure 6:
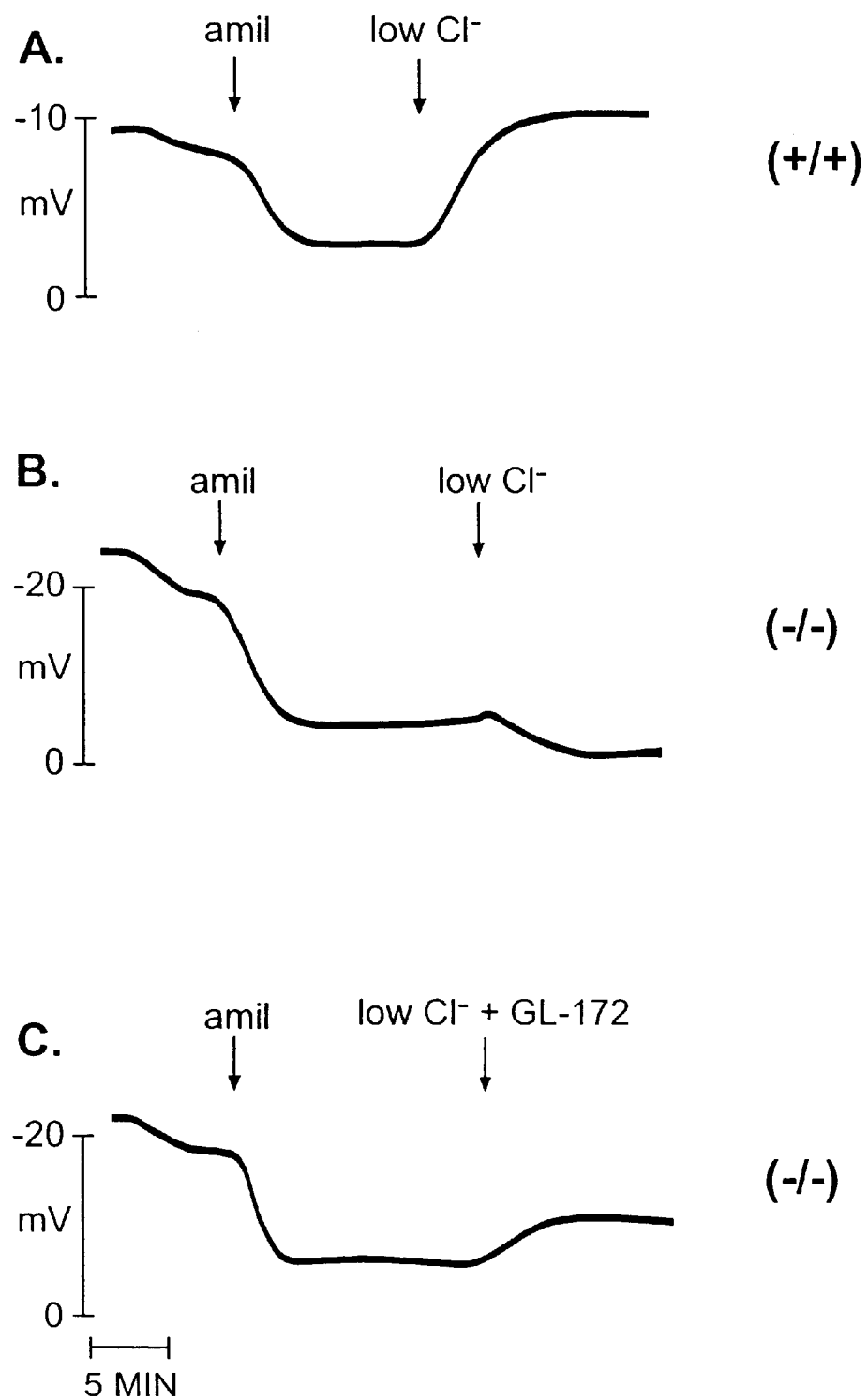
FIG. 6. GL-172 induced hyperpolarization in CF mice. Potential difference across the nasal epithelia was measured in (A) wild type (+/+) mice and (B) homozygous FABP-CFTR bitransgenic (−/−) CF mice under basal conditions, following administration of amiloride, and Cl⁻ substitution in the presence of amiloride (low Cl⁻). (C) is a tracing from a homozygous (−/−) CF mouse that showed a hyperpolarization in response to perfusion of the low Cl- solution containing GL-172 (100 $\mu$M).
Figure 7:
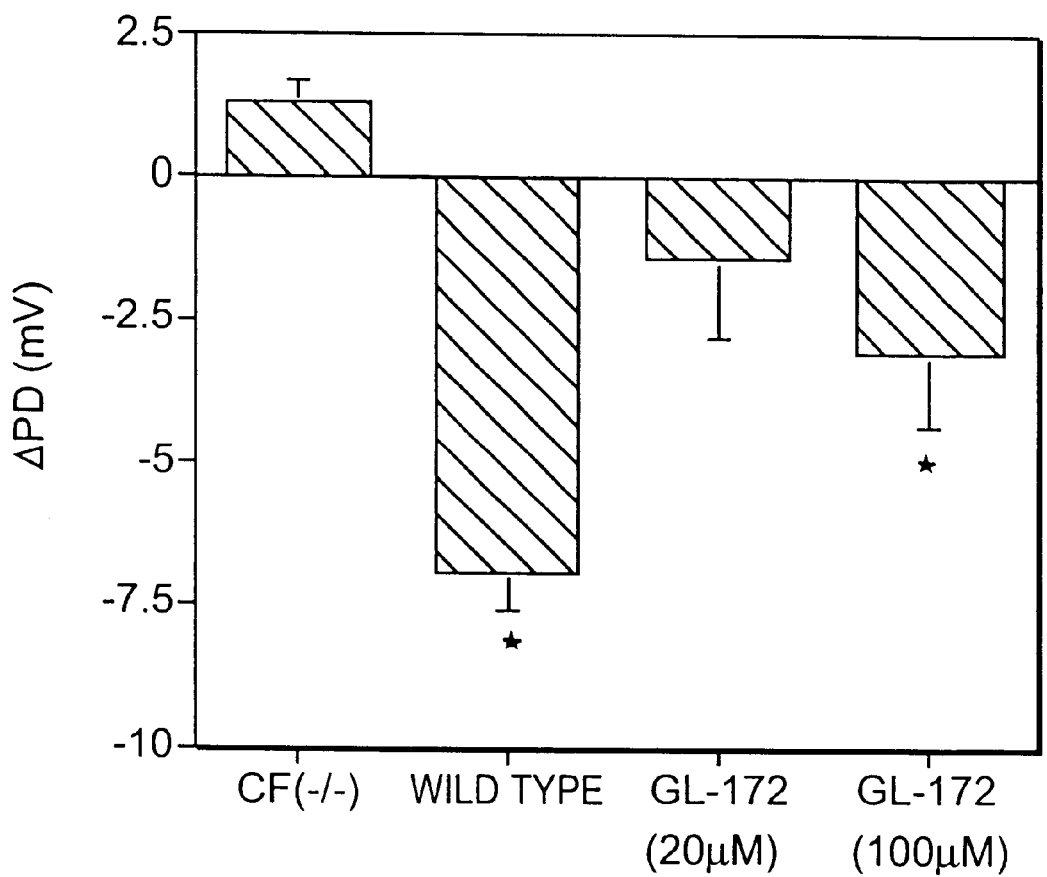
FIG. 7. Summary of GL-172 induced hyperpolarization in wild type and CF mice. Changes in potential difference ($\Delta$PD) of the nasal epithelia in response to low Cl⁻ solution with or without GL-172 were measured in the presence of amiloride addition (20 and 100 $\mu$M, respectively). Data are expressed as mean±SEM (n≧4). * indicates p<0.05 compared to CF (−/−).

FIG. 5 shows representative tracings of the basal potential difference, PD changes induced by amiloride, and PD changes in response to subsequent substitution of NaCl with Na gluconate in the presence of amiloride, in wild type (FIG. 5A) and CF (FIG. 5B) mice. Substitution of NaCl with Na-gluconate caused a small depolarization in the CF bitransgenic animals but a significant hyperpolarization in normal mice. Addition of GL-172 in the low Cl– Ringer solution induced a hyperpolarization in CF mice (FIG. 5C). In 3 out of 4 mice GL-172 (100 μM) caused a hyperpolarization (2.5, 3, and 6.5 mV, respectively). At a reduced concentration (20 mM), a hyperpolarization (4.2 mV) was only observed in 1 out of 3 animals examined. Statistical analysis (FIG. 6) indicates that the hyperpolarization response induced by GL-172 (100 μM) is significant (p<0.05).

Example 5

Whole-cell patch-clamp analysis of IBE-1 cells treated with GL-172

Whole cell patch-clamp recording

Whole cell patch-clamp recordings were performed essentially as described previously Jiang et al., *Am. J. Physiol.,* 275 (Cell Physiol. 44):C (1998); Jiang et al. *Human Gene Therapy,* 9:(July 20), (1998). Briefly, cells on coverslips were placed in a chamber mounted on a Nikon diaphot inverted microscope. Patch pipettes had resistance of 2–4 MΩ. Whole cell configuration was achieved with an additional pulse suction in order to rupture the gigaseal. The pipette solution (intracellular) at a pH of 7.4 contained: 130 mM CsCl, 20 mM TEA-Cl, 10 mM -2-hydroxylethylpiperazine-N'-2-ethanesulfonic acid (HEPES), 10 mM ethylene glycol-bis-(β-aminoethylether) N, N, N',N'-tetraacetic acid (EGTA), 10 mM Mg-ATP, and 0.1 mM LiGTP, pH 7.4. The bath solution (extracellular) also at a pH of 7.4 contained: 140 mM -methyl-D-glutamine (NMDG), 2 mM $CaCl_2$, 1 mM $MgCl_2$, 0.1 mM $CdCl_2$, 10 mM HEPES, 4 mM CsCl, and 10 mM glucose. The intracellular and extracellular solutions were designed so as to study only $Cl^-$ currents, since $Cl^-$ was the only significant permeant ion in the solutions. Aspartate was used as the replacement anion in experiments in which extracellular $Cl^-$ concentration was changed. GL-172 (1, 10 and 100 μM, dissolved in DMSO), or equal concentration of DMSO (0.5% and 1% v/v) was added to the bath solutions as indicated. Current recordings were made from the same cells before, during, and after exposure to the solutions containing the different concentrations of GL-172 or DMSO. All experiments were performed at room temperature (22° C.). Currents were filtered at 2 KHz. Data acquisition and analysis were performed using the pCLAMP 5.5.1 software (Axon Instruments, Foster City, Calif.).

Whole-cell patch-clamp analysis of IBE- cells treated with GL-172

Figure 8:
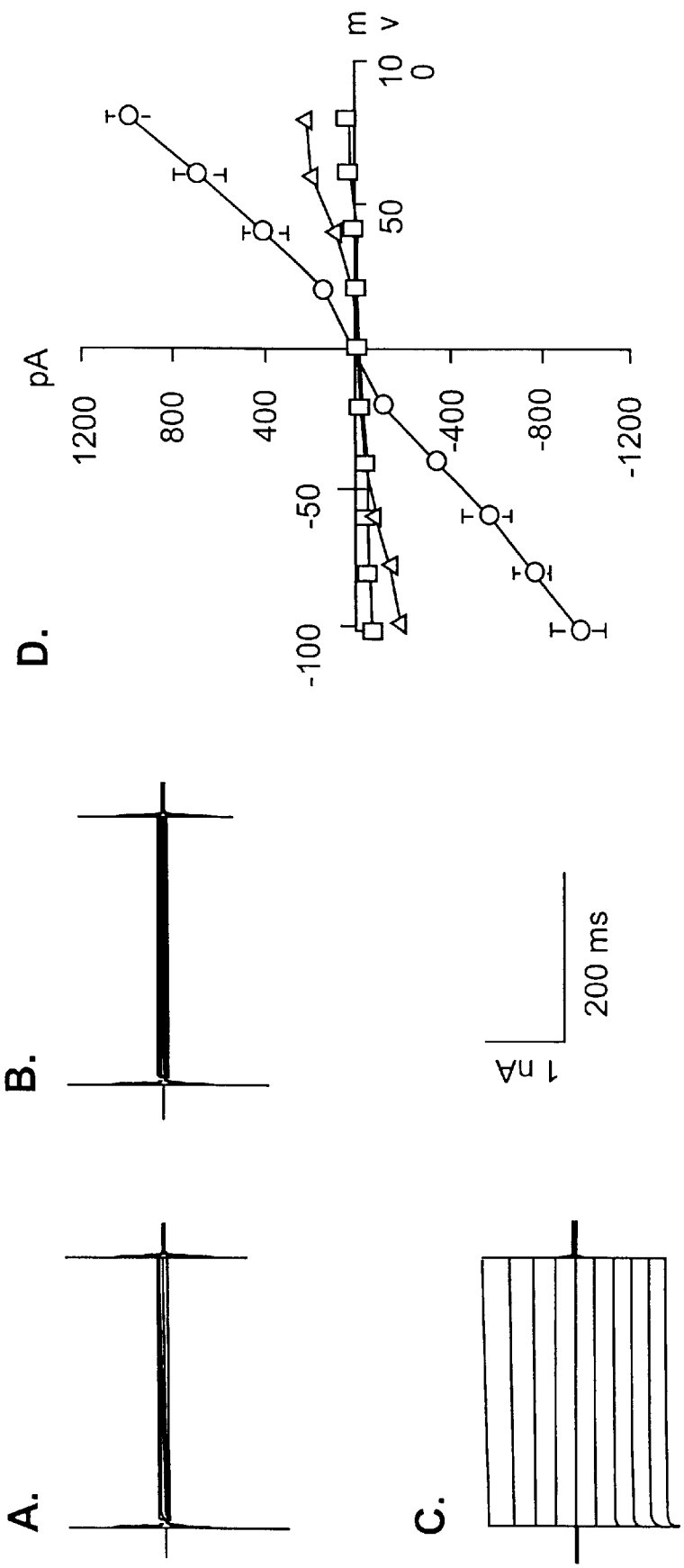
FIG. 8. Summary of whole cell patch-clamp analysis of CFT-1 cells. The currents shown are in response to voltage steps from a holding potential of 0 mV to between−100 mV and +80 mV in steps of 20 mV increment. Representative whole cell currents under basal (untreated) conditions from CFT1 cells (A) and from IBE-1 cells that had been treated with DMSO (1% v/v) (B) are shown. (C) is a recording using the same CFT1 cells as in (A) after treating the CFT1 cells with GL-172 (100 $\mu$M, dissolved in DMSO). In (D), the current-voltage relationships obtained under basal conditions (squares), after addition of 10 $\mu$M GL-172 (triangles), and following treatment with 100 $\mu$M DSG (10 $\mu$g/ml) for 48 to 72 h (circles) are summarized. The currents showed linear current voltage behavior and no time dependence. Data are presented as mean +/−SEM.

In order to confirm that the observed signals were $Cl^-$ currents, whole-cell patch-clamp experiments were performed on the CFT1 cells. FIG. 8 (panels A, B, and C) shows representative current tracings from one such experiment. In these studies, the holding potential was 0 mV (which inactivates the voltage-gated $Na^+$ and $Ca^{2+}$ channels) and the voltage was stepped from −100 mV to +80 mV in 20 mV increments to activate whole cell currents. Currents from calcium and potassium channels were minimized by omitting $K^+$ from both intra and extracellular solutions, and by inclusion of 100 μM $Cd^{2+}$ in the extracellular solution and 20 mM TEA and 10 mM EGTA in the intracellular solution. Under these conditions, there was little currents in cells untreated with GL-172 (FIG. 8A). Additionally, DMSO of up to two-fold of the solvent concentration (1% v/v) failed to activate whole cell currents (FIG. 8B).

GL-172 at a concentration of 1 or 10 μM did not cause an increase in whole cell currents in any of the cells examined. However, GL-172 at a higher concentration (30 μM) induced a significant increase in whole cell currents in 30% of the cells examined. Additionally, at a concentration of 100 μM, GL-172 caused a large increase in whole cell currents in all of the cells tested (FIG. 8C). The currents were sustained for 40 min (maximum time tested) and were persistent after washout with control buffer.

Finally, the current/voltage relationship with and without GL-172 are summarized in FIG. 8D. The whole cell currents in the cells treated with GL-172 displayed a linear current-voltage relationship and were time-independent. These properties were qualitatively similar to those observed with wild type CFTR (Anderson et al, 1991).

We claim:

1. A method of generating chloride secretion from intact monolayers of epithelial cells comprising the step of administering an effective amount of a non-peptide ionophore.

2. A method of generating chloride secretion from intact monolayers of epithelial cells according to claim 1, wherein said non-peptide ionophore is chosen from the group consisting of:

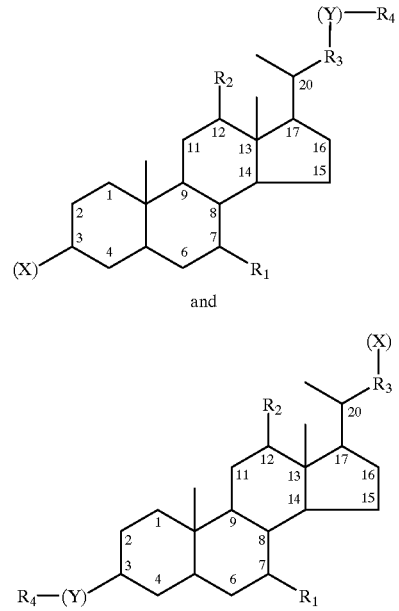

wherein:

a double bond may be present between positions 5 and 6, or between positions 7 and 8, or between positions 5 and 6, and 7 and 8 simultaneously;

($R_1$) is chosen from H and OH;

($R_2$) is chosen from H and OH;

($R_3$) is chosen from saturated and unsaturated, branched and unbranched, alkyl chains or is absent;

(X) is chosen from $SO_4^-$, $PO_4^{2-}$, $HOPO_3^-$, and $CO_2^-$;

(Y) is a linking group or is absent; and ($R_4$) is an chosen from amines, alkylamines, and polyalkylamines.

3. A method of generating chloride secretion from intact monolayers of epithelial cells according to claim 2, wherein said non-peptide ionophore is:

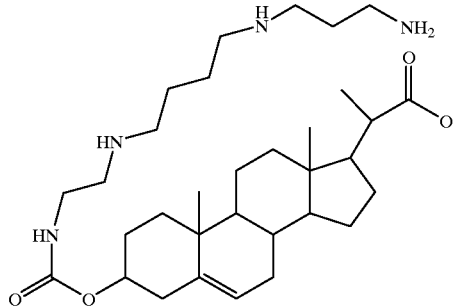

4. A method of generating chloride secretion from intact monolayers of epithelial cells according to claim 2, wherein said ($R_3$) is $(CH_x)_m$, wherein said x is chosen from 0, 1, and 2, and said m is chosen from 1 to 10.

5. A method of generating chloride secretion from intact monolayers of epithelial cells according to claim 1, wherein said non-peptide ionophore is chosen from the group consisting of:

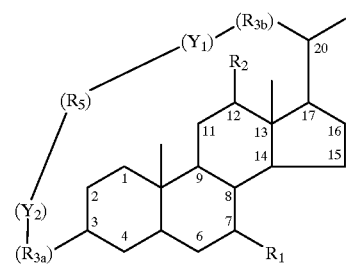

wherein:
  a double bond may be present between positions 5 and 6, or between positions 7 and 8, or between positions 5 and 6, and 7 and 8 simultaneously;
  ($R_1$) is chosen from H and OH;
  ($R_2$) is chosen from H and OH;
  ($R_{3a}$) and ($R_{3b}$) are chosen from saturated and unsaturated, branched and unbranched alkyl chains;
  ($Y_1$) and ($Y_2$) are linking groups or are absent; and
  ($R_5$) is chosen from alkylamines and polyalkylamines.

6. A method of generating chloride secretion from intact monolayers of epithelial cells according to claim 5, wherein said ($R_{3a}$) and ($R_{3b}$) are $(CH_x)_m$, wherein said x is chosen from 0, 1, and 2, and m is chosen from 1 to 10.

7. A method of generating chloride secretion from intact monolayers of epithelial cells according to claim 1, wherein said ionophore is chosen from the group consisting of:

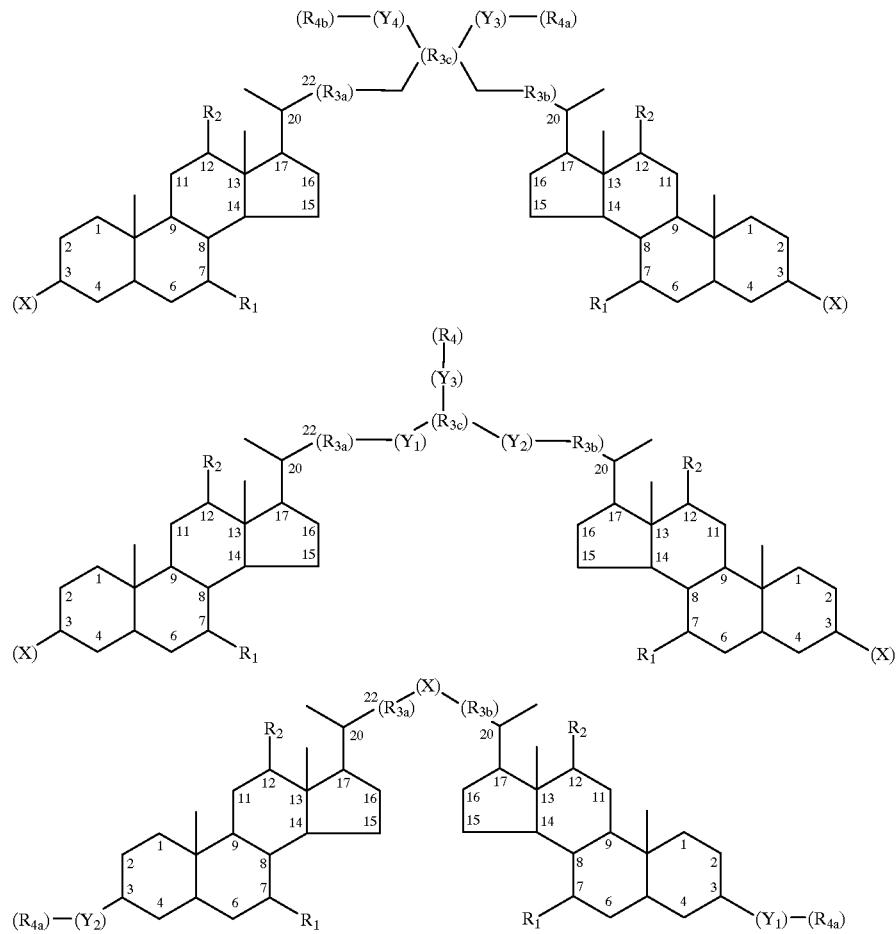

wherein:

a double bond may be present between positions 5 and 6, or between positions 7 and 8, or between positions 5 and 6, and 7 and 8 simultaneously;

(X) is chosen from $SO_4^-$, $PO_4^{2-}$, $HOPO_3^-$, and $CO_2^-$; and

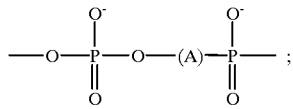

($R_1$) is chosen from H and OH;
($R_2$) is chosen from H and OH;
($R_{3a}$),($R_{3b}$) and ($R_{3c}$) are chosen from saturated and unsaturated, branched and unbranched, alkyl chains;
($Y_1$), ($Y_2$), ($Y_3$) and ($Y_4$) are linking groups or are absent; and

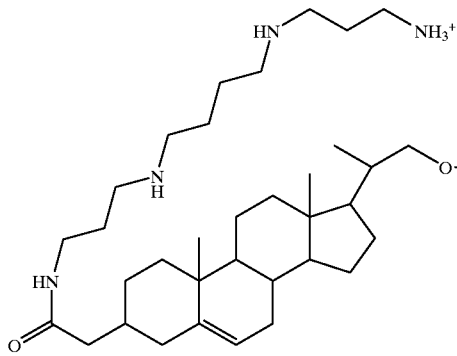

($R_4$)$_1$ ($R_{4a}$), and ($R_{4b}$) are chosen from alkylamines and polykylamines; and (A) is —$(CH_2)_m$-O-, wherein m is chosen from 2 to 10, or (A) is absent.

8. A method of generating chloride secretion from intact monolayers of epithelial cells according to claim 7, wherein said ($R_{3a}$) and ($R_{3b}$) are $(CH_x)_m$, wherein said x is chosen from 0, 1, and 2, and m is chosen from 1 to 10.

9. A method of generating chloride secretion from intact monolayers of epithelial cells according to claim 7, wherein said ($R_{3c}$) is chosen from:

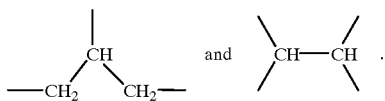

10. A method of generating chloride secretion from intact monolayers of epithelial cells according to claim 7 wherein said (X) is:

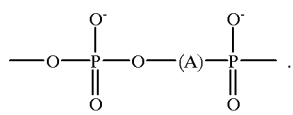

wherein (A) is —$(CH_2)_m$-O- and m is chosen from 2 to 10, pr (A) is absent.

11. A method of generating chloride secretion from intact monolayers of epithelial cells according to claim 2, wherein said non-peptide ionophore is:

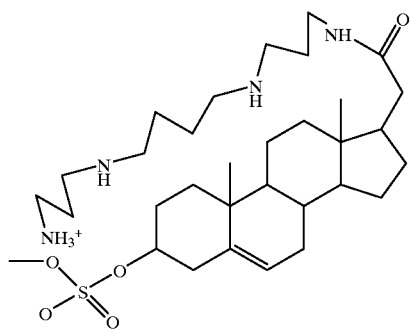

12. A method of generating chloride secretion from intact monolayers of epithelial cells according to claim 7 wherein said non-peptide ionophore is:

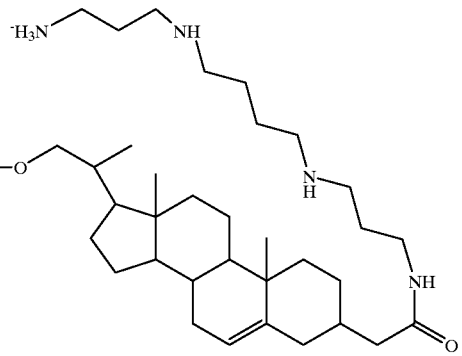

13. A method of generating chloride secretion from intact monolayers of epithelial cells according to claim 2, wherein said (Y), if present, is: >C=O; —$CH_2$—O—C(=O)—; —O—C(=O)—; —$CH_2$—NH—; —C(=O)—NH—; —NH—C(=O)—O—; —$(CH_2)_2$—; —$(CH_2)_3$—; —$(CH_2)$—(C=O)—; —$(CH_2)_n$—NH—(C=O)— wherein n is preferably 4 or less; glycinyl, alanyl, beta-alanyl, and serinyl.

14. A method of generating chloride secretion from intact monolayers of epithelial cells according to claim 5, wherein said ($Y_1$) and ($Y_2$), if present, are: >C=O; —$CH_2$—O—C(=O)—; —O—C(=O)—; —$CH_2$—NH—; —C(=O)—NH—; —NH—C(=O)—O—; —$(CH_2)_2$—; —$(CH_2)_3$—; —$(CH_2)$—(C=O)—; —$(CH_2)_n$—NH—(C=O)— wherein n is preferably 4 or less; glycinyl, alanyl, betaalanyl, or serinyl.

15. A method of generating chloride secretion from intact monolayers of epithelial cells according to claim 5, wherein said ($Y_1$), ($Y_2$), ($Y_3$) and ($Y_4$), if present, are: >C=O; —$CH_2$—O—C(=O)—; —O—C(=O)—; —$CH_2$—NH—; —C(=O)—NH—; —NH—C(=O)—O—; —$(CH_2)_2$—; —$(CH_2)_3$—; —$(CH_2)$—(C=O)—; —$(CH_2)_n$—NH—(C=O)— wherein n is preferably 4 or less; glycinyl, alanyl, beta-alanyl, and serinyl.

* * * * *

UNITED STATES PATENT AND TRADEMARK OFFICE
CERTIFICATE OF CORRECTION

PATENT NO. : 6,323,191 B1
DATED : November 27, 2001
INVENTOR(S) : David J. Harris et al.

It is certified that error appears in the above-identified patent and that said Letters Patent is hereby corrected as shown below:

Title page,
Item [75], inventors, "Wellesley;" should read -- Wellesley, all of MA; --.
"Cambridge, all of MA" should read -- New York, NY --.

Item [57], ABSTRACT,
Line 10, "transport lonophores" should read -- transport. Ionophores --.

Column 18,
Line 65, "is an chosen" should read -- is chosen --.

Column 20,
After line 28, first structure, "$(Y_1)$" and "$(Y_2)$" should be inserted as shown:

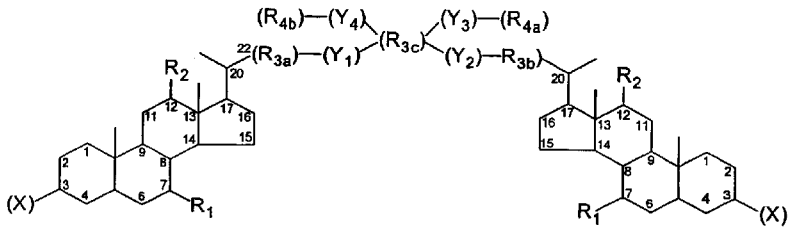

Column 21,
Line 37, "$(R_4)_1$" should read -- $(R_4)$, --.
Line 38, "polykylamines" should read -- polyalkylamines --.
Line 39, "2to" should read -- 2 to --.
Line 54, "7 wherein" should read -- 7, wherein --.
Structure after line 55, "O" should be inserted to the far right as shown:

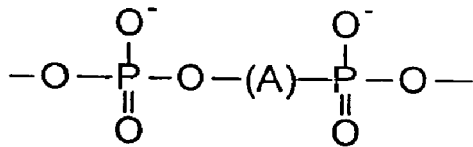

Structure after line 55, "." should read -- --
Line 64, "pr" should read -- or --.

UNITED STATES PATENT AND TRADEMARK OFFICE
CERTIFICATE OF CORRECTION

PATENT NO.    : 6,323,191 B1
DATED         : November 27, 2001
INVENTOR(S)   : David J. Harris et al.

It is certified that error appears in the above-identified patent and that said Letters Patent is hereby corrected as shown below:

Column 22,
Line 18, "7 wherein" should read -- 7, wherein --.
Line 54, "betaalanyl" should read -- beta-alanyl --.

Signed and Sealed this

Thirteenth Day of August, 2002

*Attest:*

*Attesting Officer*

JAMES E. ROGAN
*Director of the United States Patent and Trademark Office*